United States Patent [19]

Bouzard et al.

[11]  4,053,360
[45]  Oct. 11, 1977

[54] ENZYMATIC PREPARATION OF 6-D-(—)-α-AMINO-α-(P-HYDROXY-PHENYLACETAMINO)PENICILLIN ACID

[75] Inventors: Daniel Bouzard, Franconville; Abraham Weber, Paris, both of France

[73] Assignee: Bristol-Myers Company, New York, N.Y.

[21] Appl. No.: 580,991

[22] Filed: May 27, 1975

[30] Foreign Application Priority Data

June 5, 1974  United Kingdom ............... 24848/74
Mar. 19, 1975  United Kingdom ............... 50016/75

[51] Int. Cl.$^2$ ........................... C12B 1/00; C12D 1/00
[52] U.S. Cl. .................................. 195/29; 260/239.1; 195/30

[58] Field of Search ....................... 260/239.1, 243 C; 195/29, 369, 30

[56] References Cited

U.S. PATENT DOCUMENTS

| 3,202,656 | 8/1965 | Abraham et al. | 260/243 C |
| 3,436,310 | 4/1969 | Arnold et al. | 260/243 C |
| 3,532,694 | 10/1970 | Somerfield et al. | 260/243 C |

Primary Examiner—Gerald A. Schwartz
Attorney, Agent, or Firm—Herbert W. Taylor, Jr.

[57] ABSTRACT

This invention relates to a novel α-aminoα-(p-acyloxyphenyl)acetamidopenicillanic acid which is useful as an antibacterial agent, and also to a novel process for the production of 6-D-(—)α-amino-α-(p-hydroxyphenylacetamido)penicillanic acid (also known as amoxycillin).

3 Claims, No Drawings

ENZYMATIC PREPARATION OF 6-D-(−)-α-AMINO-α-(P-HYDROXY-PHENYLACETAMINO)PENICILLIN ACID

BACKGROUND OF THE INVENTION

1. Field of the Invention

The chemical compound of the present invention is an antibacterial agent of the class commonly called penicillins.

2. Description of the Prior Art

U.S. Pat. No. 2,985,648 relates to α-aminobenzylpenicillins and discloses a general formula for such penicillins which includes, inter alia, lower alkanoyloxy substituents on the benzene ring. This document does not give any more specific details of compounds so substituted, and no specific examples are given of their preparation. The document indicates that the α-aminobenzylpenicillins exist in various optical forms and specific examples are given of the preparation of both D- and L- forms.

U.S. Pat. No. 3,520,876 refers also to the same general formula for α-aminobenzylpenicillins as given in U.S. Pat. No. 2,985,648 and discloses, in a list of 21 compounds, 6-α-amino-4-acetoxy-benzylpenicillanic acid (or 6-α-amino-α-(p-acetoxyphenylacetamido)penicillanic acid). U.S. Pat. No. 3,520,876 gives no indication whether any particular optical isomer of this compound was prepared, and no details of its antibacterial activity are given.

SUMMARY OF THE INVENTION

We have now discovered that the compound 6-D-(−)α-amino-α-(p-acetoxyphenylacetamido)penicillanic acid has particular value for use as an antibacterial agent and in one aspect of the invention there is provided the compound 6-D-(−)α-amino-α-(p-acetoxyphenylacetamido)penicillanic acid, or a pharmaceutically acceptable salt thereof, when substantially free of the L-(+) isomer.

The pharmaceutically acceptable salts referred to above include the nontoxic carboxylic acid salts, e.g. nontoxic metallic salts such as sodium, potassium, calcium and aluminium, the ammonium salt and salts with nontoxic amines, e.g. trialkylamines, procaine, dibenzylamine, N-benzyl-β-phenethylamine, 1-ephenamine, N,N'-dibenzylethylenediamine, N-alkylpiperidine and other amines which are used to form salts of penicillins. Also included within the definition of pharmaceutically acceptable salts are the nontoxic acid addition salts (amine salts), e.g. salts with mineral acids such as hydrochloric, hydrobromic, hydroiodic, phosphoric, sulfuric and salts with organic acids such as maleic, acetic, citric, oxalic, succinic, benzoic, tartaric, fumaric, mandelic ascorbic and malic.

The present invention also includes a process for the preparation of 6-D-(−)α-amino-α-(p-acetoxyphenylacetamido) penicillanic acid, or a pharmaceutically acceptable salt thereof, substantially free of the L-(+) isomer, which process comprises reacting a compound of the formula

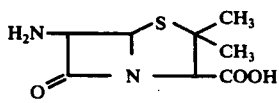

(I)

or a silyl ester or salt thereof with an acylating agent of the formula

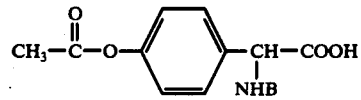

(II)

in which B is an amino-protecting group, and removing the amino-protecting group to produce the named compound or a pharmaceutically acceptable salt thereof, and, if desired, either before or after removal of B, converting by methods known per se the product in the form of the free acid or silyl ester or salt thereof to the corresponding free acid or pharmaceutically acceptable salt thereof; said compound of formula (II) being in the D-(−) form, substantially free of the L-(+) isomer.

In the preparation of the novel penicillin compounds of the present invention, a corresponding 6-aminopenicillanic acid compound of formula (I) or silyl ester or salt thereof is acylated by known methods with the appropriate acylating agent of formula (II).

The compound (I) may, if desired, be converted, prior to the acylation reaction, to a silyl ester or acid addition salt thereof. The silyl esters may be prepared by methods described in the literature, e.g. U.S. Pat. No. 3,249,622. The silyl ester group may be removed following the acylation reaction by hydrolysis.

Prior to the acylation reaction the amino group of the acylation agent II may be protected by a conventional amino-blocking group B, which may be readily removed at the conclusion of the reaction by methods known per se. Examples of suitable amino-protecting or blocking groups include t-butoxycarbonyl, carbobenzyloxy, 2-hydroxy-1-naphthcarbonyl, trichloroethoxycarbonyl, 2-ethoxycarbonyl-2-methylvinyl and 2-methoxycarbonyl-1-methylvinyl. A particularly valuable blocking group is a proton, as in the compound of the formula:

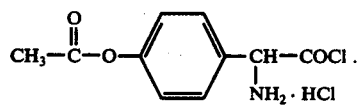

For example, following the acylation coupling reaction, it can be easily removed by neutralization. Obviously other functionally equivalent blocking groups for an amino group can be used and such groups are considered within the scope of this invention.

Acylation of a 6-amino group of a penicillin is a well-known reaction and any of the functional equivalents of formula (II) commonly used as acylating agents for primary amino groups may be employed. Examples of suitable acylating derivatives of the acid of formula (II) include the corresponding acid anhydrides, mixed anhydrides, e.g. alkoxyformic anhydrides, acid halides, acid azides, active esters and active thioesters. The free acid of formula (II) may be coupled with compound (I) after first reacting said free acid with N,N'-dimethylchloroforminium chloride or by the use of enzymes or of an N,N'-carbonyldiimidazole or an N,N'-carbonyldi-triazole or a carbodiimide reagent, e.g. N,N-diisopropylcarbodiimide. N,N'-dicyclohexylcarbodiimide or N-cyclohexylcarbodiimide or N-cyclohexyl-N'-(2-morphilinoethyl) carbodiimide or of an alkylylamine reagent or of an isoxasolium salt reagent. Another equivalent of the free acid is a corresponding azolide, i.e. an amide of the corresponding acid whose amide nitrogen is a member of a quasiaromatic five membered ring containing at least two nitrogen atoms, i.e. imidazole, pyrazole, the triazoles, benzimidazole, benzotriazole and their substituted derivatives. Another reactive derivative of the phenylglycine acid of formula (II) is the N-carboxy anhydride (Leuch's anhydride). In this structure the group which activates the carboxyl group also serves to protect the amino group. A particularly preferred acylating agent is the D-(—) isomer of the acid chloride hydrochloride of the formula

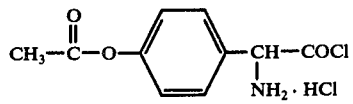

which also serves a dual function of carboxyl activation and amino protection. Mention was made above of the use of enzymes to couple the free acid with its blocked amino group with compound (I). Included in the scope of such processes are the use of an ester, e.g. the methyl ester, of that free acid with enzymes provided by various microorganisms, e.g. those described by T. Takahashi et al., *J. Amer. Chem. Soc.*, 94(11), 4035–4037 (1972) and by T. Nara et al., *J. Antibiotics* (Japan), 24(5), 321–323 (1971) and in West Germany 2,216,113.

The particular process conditions, e.g. temperature, solvent, reaction time, etc. selected for the coupling reaction are determined by the nature of the acylation method used and are known to those skilled in the art. Generally it is useful to add an organic tertiary amine, e.g. triethylamine, N,N-dimethylaniline, ethylpiperidine, 2,6-lutidine or quinoline, to serve as a proton acceptor or salt-forming agent.

The compounds of the present invention may be isolated in any of the ways customarily employed for the isolation of similar penicillins. Thus, the product may be obtained as the neutral molecule although this is probably more accurately represented as the zwitterion, or it may be isolated as a salt. Formation of the desired pharmaceutically acceptable carboxylic acid or acid addition salt is carried out by known methods, e.g. reaction of the acid with an appropriate base or acid.

At the conclusion of the acylation reaction the product obtained may be converted (before or after removal of the amino-protecting group) by methods known per se to the desired form of the novel product. For example, the product in the form of a silyl ester or salt thereof may be converted to the free acid product or pharmaceutically acceptable salt thereof by removal of the silyl ester group, e.g. by hydrolysis.

The pharmaceutically active compounds of the present invention are potent antibacterial agents useful in the treatment of infectious diseases in poultry and animals, including man, caused by many Gram-positive and Gram-negative bacteria. The active compounds are also of value as nutritional supplements in animal feeds and as agents for the treatment of mastitis in cattle. The preferred compounds have also been unexpectedly found to be efficiently absorbed upon oral administration.

The novel medicaments provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or emulsions. In the treatment of bacterial infections in man, the compounds of this invention may be administered parenterally in an amount of from about 5 to 200 mg./kg.day in divided dosage, e.g. 3 to 4 times a day. They are administered in dosage units containing e.g. 125, 250 or 500 mg. of active ingredient with suitable physiologically acceptable carriers or excipients.

The following illustrates the preparation of starting materials used in the production of the novel compound of the invention, as described in Example 1 hereafter.

STARTING MATERIALS

Preparation of
D(—)α-amino-α-(p-acetoxyphenyl)acetic acid

Method A (in acetic acid as solvent)

203.5 g. (1 Mole) of D(—)p-hydroxyphenylglycine hydrochloride, 800 ml. of acetic acid and 314 g. (4 Moles) of acetyl chloride were stirred for 48 hours at room temperature. The solid was collected, washed three times with acetone (3 × 250 ml). and twice with ethanol (2 × 250 ml.) and dried at 40°. Yield 210 g. 85.4%). This hydrochloride was dissolved in 3.0 l. of water; the solution was cooled to +5° to 10° C. and the pH adjusted to 4.5 with 20% NH4OH. The suspension was stirred for 1 hour at 5° C. and the solid collected, washed twice with water and twice with acetone, and dried at 40° C. Yield 133 g. (64% from D(—)p-hydroxyphenylglycine). D (1% HCl N/$_{10}$ = —104.5.

Method B (in methylene chloride)

4.07 g. (0.02 Mole) of D(—)p-hydroxyphenylglycine hydrochloride, 30 ml. of methylene chloride and 6.28 g. (0.08 Mole) of acetyl chloride were stirred for 48 hours at room temperature. The solid was collected, washed twice with acetone and twice with ethanol. Yield 4.17 g. (84.5%).

Anal. Cl = 14.8 (calculated acid)

Method C (in trifluoroacetic acid)

1.67 g. (0.01 Mole) of D(—)p-hydroxyphenylglycine was added with stirring, to 10 ml. of trifluoroacetic acid at room temperature. After dissolution, 1.57 g. (0.02 Mole) of acetyl chloride was added. After a slightly exothermic reaction, a solid appeared. The suspension was stirred for 1.5 hours at room temperature and the trifluoroacetic acid was removed in vacuum. The remaining solid was collected, washed with methylene chloride and with ethanol. The D(—)α-amino-α-(p-acetoxyphenyl)acetic acid was identical to that prepared by Methods A or B.

Yield: 1.9 g. (75%)

Preparation of
D(—)α-amino-α-(p-acetoxyphenyl)acetyl chloride hydrochloride 83.6 g. (0.40 Mole) of D(—)α-amino-α-(p-acetoxyphenyl)acetic acid and 1.25 l. of anhydrous methylene chloride were cooled to —5° C. with stirring. Then 152 g. of phosphorous pentachloride were slowly added followed by 4 ml. of dimethyl formamide. The mixture was stirred 4 hours at 0° C. The solid was collected, washed with anhydrous methylene chloride and vacuum dried at room temperature.

Yield: 61 g. (57.5%)

Anal. Total chlorine = 27.2% (Theory 26.9%)

DESCRIPTION OF THE PREFERRED EMBODIMENTS

The following example is given in illustration of, but not in limitation of, the present invention. All temperatures are in degrees Centigrade. 6-Aminopenicillanic acid is abbreviated as 6-APA.

EXAMPLE 1

6-D-(—)α-amino-α-(p-acetoxyphenylacetamido)-penicillanic acid or acetoxy-ampicillin - or RN 1395

Method A: Anhydrous Process 15.27 g. (0.071 Mole) of 6-APA were stirred in 500 ml. of anhydrous methylene chloride; 120 ml. of methylene chloride were distilled off and 11.8 ml. of hexamethyldisilazane were added. The mixture was stirred and refluxed for 20 hours (after about 10–15 hours all the 6-APA was run in solution). The above solution was cooled to 0 ° C, and 120 ml. of methylene chloride followed by the addition of 9.5 ml. of dimethylaniline and 7 ml. of a solution of dimethylaniline hydrochloride in methylene chloride (30%). Then 20 g. (0.0756 Mole) of D(—)α-amino-α-(p-acetoxyphenyl)acetyl chloride, hydrochloride were added in small portions (≃1½ hour) at +20° C. and allowed to stand overnight at +5° C. Then 5 ml. of methanol followed by 240 ml. of water were added. The pH was adjusted at 2.5 with triethylamine and the mixture was filtered through a Celite pad; the pH was then checked and the aqueous phase was separated, washed twice (2 × 150 ml.) with methylene chloride and treated with charcoal. The solution was adjusted to pH 4.5 and vacuum concentrated to a volume of ≃150 ml. The suspension was allowed to stand overnight at +5° C. and the solid collected and washed with water and acetone, and dried at 40° C., to provide the named product substantially free of the L-(+) isomer.

Yield = ≃30% (of a 85–90% pure material)
$\alpha_D$(0.5% HCl N/10) = +205.5
Elemental analysis for a trihydrate

|   | Theor. | Found |
|---|--------|-------|
| C | 46.85 | 47.17 |
| H | 5.89 | 5.72 |
| N | 9.10 | 9.02 |
| S | 6.93 | 7.27 |
| $H_2O$ | 11.7 | 11.33 (KF) and 10.77 (T G A) |

N M R is consistent with assigned structure.
Iodometric assay (against ampicillin standard) = 738 mcg./ml.

Method B: Wet process 10.8 g. (0.05 Mole) of 6-APA were dissolved in 45 ml. of water and 11.7 ml. HCl 6N; 300 ml. of acetone were added and the mixture cooled to −5° C. Then 7.4 g. (0.028 Mole) of D(—)α-amino-α-(p-acetoxyphenyl)acetyl chloride hydrochloride were added in small portions and the pH kept constant at 1.4–1.6 by triethylamine addition.

The second fraction of chloride hydrochloride was added at pH 1.2–1.4. After 1 hour at −5° C., the acetone was vacuum removed and the pH of the solution adjusted to 4.3–4.5. The solid material was collected and discarded. The mother liquors were seeded and allowed to crystallize overnight at +5° C. The RN 1395 was collected, carefully washed with a little water and with acetone and dried at 40° C. Yield: 2.0 g. (9%). The product obtained was identical to the one prepared by Method A.

Biological Data

Table I shows comparative MIC data for amoxycillin (BL-P1410:p-hydroxy analogue of ampicillin), and p-acetoxyampicillin (RN-1395). Minimal inhibitory concentrations were determined by the 2-fold broth dilution method utilizing equimolar concentrations of each compound.

Table II and the accompanying FIGS. I and II show comparative blood level data in rats and dogs when administering amoxycillin (BL-P1410) and p-acetoxyampicillin (RN-1395). Table III summarises results obtained from the FIGS. I and II.

As will be observed from the biological data, p-acetoxyampicillin and amoxycillin have similar MIC properties, but p-acetoxyampicillin has surprisingly superior blood level properties.

TABLE I

| | MIC (mg./ml.) | | |
|---|---|---|---|
| Nutrient Broth Organisms | | Amoxycillin (BL-P1410) | p-acetoxy ampicillin RN 1395 |
| D. pneumoniae* (10-3)** | A9585 | .008 | .008 |
| Str. pyogenes* (10-3)** | A9604 | .008 | .008 |
| S. aureus Smith (10-4) | A9537 | .06 | 0.13 |
| S. aureus +5% serum (10-4) | A9537 | .06 | 0.13 |
| S. a8reus BX1633 (10-3) | A9606 | 8 | 8 |
| S. aureus BX1633 (10-2) | A9606 | >125 | >125 |
| S. aureus Meth-Res (10-3) | A15097 | 63 | 63 |
| Sal. enteritidis (10-4) | A9531 | 0.13 | 0.13 |
| E. coli Juhl (10-4) | A15119 | 2 | 4 |
| E. coli (10-4) | A9675 | 32 | 32 |
| K. pneumoniae (10-4) | A9977 | 0.3 | 0.3 |
| K. pneumoniae (10-4) | A15130 | 125 | >125 |
| Pr. mirabilis (10-4) | A9900 | 0.3 | 0.6 |
| Pr. morganii (10-4) | A15153 | 125 | >125 |
| Ps. aeruginosa (10-4) | A9843A | >125 | >125 |
| Ser. marcescens (10-4) | A20019 | 32 | 63 |
| Ent. cloacae (10-4) | A9656 | >125 | >125 |
| Ent. closcae (10-4) | A9657 | 63 | 63 |
| Ent. cloacae (10-4) | A9659 | 63 | >125 |

*45 AAB + 5% serum + 50% NB
**Dilution of overnight broth culture

TABLE II

| | | Blood levels in rats (mcg/ml) 100 mg/Kg - oral route | | | | | |
|---|---|---|---|---|---|---|---|
| | | hours | | | | | |
| Compound | Sex | 0.5 | 1 | 1.5 | 2 | 4 | 6 |
| RN 1395 | M | 15.1 | 20.2 | 21.8 | 18.9 | 2.8 | 0.5 |
| | M | 22.4 | 23.0 | 20.2 | 18.6 | 2.9 | 0.8 |
| | M | 14.2 | 18.9 | 19.5 | 12.2 | 6.1 | 0.5 |
| | F | 12.2 | 21.8 | 20.7 | 17.3 | 3.6 | 0.8 |
| | F | 18.9 | 23.0 | 23.0 | 18.9 | 2.9 | 0.7 |
| | F | 14.3 | 22.4 | 20.7 | 18.6 | 3.5 | 0.4 |
| Average | | 16.18 | 21.55 | 20.98 | 17.41 | 3.63 | 0.61 |
| BL-P1410 | M | 16.0 | 23.0 | 14.3 | 12.2 | 2.9 | 0.2 |
| | M | 17.9 | 16.9 | 16.4 | 13.4 | 4.1 | 0.6 |
| | M | 18.6 | 15.5 | 16.4 | 11.0 | 3.3 | 0.5 |
| | F | 16.9 | 19.8 | 13.4 | 11.0 | 2.6 | 0.6 |
| | F | 17.7 | 15.6 | 13.4 | 15.1 | 3.4 | 0.2 |
| | F | 16.8 | 22.4 | 12.5 | 12.5 | 2.6 | 0.5 |
| Average | | 17.31 | 18.86 | 14.40 | 12.50 | 3.15 | 0.43 |

TABLE III

|  |  | RN 1395<br>DQ IV 148<br>rats orally<br>100 mg/Kg | BL-P1410<br>PR 4<br>rats orally<br>100 mg/Kg | Statistics<br>t.test |
|---|---|---|---|---|
| Average serum concentration at (mcg/ml) | 0 hours | — | — | n.s.* |
|  | 0.5 hours | 16.18 | 17.31 | $p > 0.05$ |
|  | 1 hour | 21.55 | 18.86 | $p > 0.01$ |
|  | 1.5 hours | 20.98 | 14.40 | $p > 0.01$ |
|  | 2 hours | 17.41 | 12.50 |  |
|  | 4 hours | 3.63 | 3.15 | n.s. |
|  | 6 hours | 0.61 | 0.43 | n.s. |
| Peak of the average serum concentration time curve (mcg/ml) |  | 21.55 | 18.86 | $p > 0.05$ |
| Average of the individual peak serum concentration (mcg/ml) |  | 21.91 | 19.90 | $p > 0.05$ |
| Time of the peak of the average serum concentration-time curve (hours) |  | 1.0 | 1.0 | n.s. |
| Average of the individual peak times (hours) |  | 0.75 | 1.16 | — |
| Average of the areas under the individual serum concentration-time curve $\frac{mcg}{ml} \times hours$ | 0–6 hours | 58.99 | 47.68 | $p < 0.001$ |
| Urinary elimination at (mg) | 0–3 hours | 5.06 | 4.53 |  |
|  | 3–6 hours | 1.11 | 0.90 |  |
|  | 0–6 hours | 6.17 | 5.43 |  |
| Urinary elimination in per cent of the absorbed doses | 0–6 hours | 43.7 | 39.9 | $p > 0.05$ |

In addition to the above, the compounds of the invention are also valuable as intermediates for the preparation of the corresponding p-hydroxy compounds which are known to be potent antibacterial agents useful in the treatment of infectious diseases in poultry and animals, including man, caused by many Gram-positive and Gram-negative bacteria.

We have found that 6-D-(—)α-amino-α-(p-acetoxyphenylacetamido)penicillanic acid, although stable in normal saline, is hydrolyzed enzymatically to the known and potent 6-D-(—)α-amino-α-(p-hydroxyphenylacetamido)penicillanic acid.

Accordingly, the present invention also provides for a novel process for preparing 6-D-(—)αamino-α-(p-hydroxyphenylacetamido)penicillanic acid, hydrate or a pharmaceutically acceptable salt thereof, which process comprises treating in an aqueous solution 6-D-(—)α-amino-α-(p-acetoxyphenylacetamido)penicillanic acid with an esterase at a pH between about 5.0 and about 7.5; isolating the product by methods known per se, and, if desired, converting by methods known per se the product in the form of the free acid or hydrate to the corresponding pharmaceutically acceptable salt thereof.

A preferred embodiment is the preparation of 6-D-(—)α-amino-α-(p-hydroxyphenylacetamido)penicillanic acid, hydrate or a pharmaceutically acceptable salt which process comprises treating in aqueous solution 6-D-(—)-α-amino-α-(p-acetoxyphenylacetamido)-penicillanic acid with an esterase selected from human serum, animal serum, citrus esterase, wheat bran, wheat germ, and bacillus subtilis at a pH between about 5.0 and about 7.5 and at a concentration of about 5 to about 10 mg./ml. of esterase per total volume of the aqueous solution; isolating the product by methods known per se, and, if desired, converting the product in the form of free acid or hydrate to the corresponding pharmaceutically acceptable salt thereof.

A commercially preferred embodiment of the present invention is the preparation of 6-D-(—)α-amino-α-(p-hydroxyphenylacetamido)penicillanic acid, hydrates or pharmaceutically acceptable salts thereof, which process comprises:

treating in an aqueous solution 6-D-(—)-α-amino-α-(p-acetoxyphenylacetamido)penicillanic acid with an esterase selected from citrus esterase, wheat bran, and wheat germ at a pH between about 5.0 and about 7.5 and at a concentration of about 5 to about 10 mg./ml. of esterase per total volume of the aqueous solution; and isolating the product by methods known per se, and, if desired, converting the product in the form of the free acid or hydrate to the corresponding pharmaceutically acceptable salt thereof.

Of special commercial interest is the process for preparing 6-D-(—)α-amino-α-(p-hydroxyphenylacetamido)penicillanic acid, hydrate or pharmaceutically acceptable salt thereof comprising:

treating in an aqueous solution 6-D-(—)-α-amino-α-(p-acetoxyphenylacetamido)penicillanic acid with the commercially available esterase, coarse wheat bran, at a pH between 5.5 and 6.0 or optionally in the presence of a buffer at a pH of 7.0 at a concentration of about 10 mg./ml. of esterase per total volume of solution; and isolating the product by methods known per se, and, if desired, converting the product in the form of a free acid or hydrate to the corresponding pharmaceutically acceptable salt thereof.

The 6-D-(—)α-amino-α-(p-hydroxyphenylacetamido)penicillanic acid (amoxycillin) prepared by the instant invention is known to be a potent antibacterial agent useful in the treatment of infectious diseases in poultry and animals, including man, caused by many Gram-positive and Gram-negative bacteria.

The following examples illustrate the preparation of amoxycillin according to the invention.

EXAMPLE A

Solutions of 0.5 mg./ml. of 6-D-(—)α-amino-α-(p-acetoxyphenylacetamido)penicillanic acid (p-acetoxyampicillin) in normal saline and in human serum were prepared. Standard solutions of 0.5 mg./ml. of 6-D-

(—)α-amino-α-(p-hydroxyphenylacetamido)penicillanic acid (p-hydroxyampicillin) were also prepared in both normal saline and human serum.

All the above solutions were incubated at 37° C. with shaking and sampled for chromatography at time intervals of 0, 2, 4, 8 and 24 hours. The solutions, approximately 5 microliters per strip, were spotted on Whatman No. 1 half-inch strips which were dried and developed in a solvent system containing 80 parts butylacetate; 15 parts n-butanol; 40 parts acetic acid; and 24 parts water. The strips were then bioautographed on plates seeded with bacillus subtilis at a pH of 6.0.

The biochromatograms indicated that p-acetoxyampicillin is quickly hydrolyzed to the p-hydroxy form in human serum but appears stable in normal saline.

EXAMPLE B

The following solutions were prepared:
0.5 mg./ml. of 6-D-(—)α-amino-α-(p-acetoxyphenylacetamido) penicillanic acid (p-acetoxyampicillin) in saline;
0.5 mg./ml. of p-actoxyampicillin in a solution of citrus esterase diluted tenfold with 0.1 M. potassium phosphate buffer to maintain the pH at 7.0; and
0.5 mg./ml. of p-acetoxyampicillin in a 10 mg./ml. solution of coarse wheat bran (Shiloh) containing 0.1 m. potassium phosphate buffer.

All the above solutions were incubated at 37° C. with shaking and sampled for chromatography as described in Example A.

These biochromatograms indicated that p-acetoxyampicillin is stable in saline but quickly hydrolyzed to the p-hydroxy form with both citrus esterase and bran esterase.

EXAMPLE C

The following reaction mixtures were prepared, shaken at 28° C. and sampled at intervals of 0, ½, 1, 2, 3, 4 and 6 hours as described in Example A.
1. 25 mg. defatted bran (wheat bran obtained from Shiloh, treated with acetone and dried), 4.5 ml. of 0.1 m., pH 6.0, potassium phosphate buffer and 0.5 ml. of 5mg./ml. 6-D-(—)-α-amino-α-(p-acetoxyphenylamido)penicillanic acid (p-acetoxyampicillin) in same buffer.
2. 25 mg. defatted bran, 4.5 ml. of 0.1 m. pH 7.0, potassium phosphate buffer and 0.5 ml of 5 mg./ml. p-acetoxyampicillin in same buffer.
3. 25 mg. defatted bran, 4.5 ml. of 0.1 M., pH 7.5, potassium phosphate buffer and 0.5 ml. of 5 mg./ml. p-acetoxyampicillin in same buffer.
4. 50 mg. defatted bran, 4.5 ml of 0.1 M., pH 6.0, potassium phosphate buffer and 0.5 ml. of 5 mg./ml. p-acetoxyampicillin in same buffer.
5. 50 mg. defatted bran, 4.5 ml. of 0.1 M., pH 7.0, potassium phosphate buffer and 0.5 ml. of 5 mg./ml. p-acetoxyampicillin in same buffer.
6. 50 mg. defatted bran, 4.5 ml. of 0.1 M., pH 7.5, potassium phosphate buffer and 0.5 ml. of 5 mg./ml. p-acetoxyampicillin in same buffer.

The results of the biochromatograms are shown in Table IV.

TABLE IV

| Reaction No. | % Conversion to p-hydroxyampicillin Reaction Time (hours) | | | | | | | |
|---|---|---|---|---|---|---|---|---|
| | 0 | ½ | 1 | 2 | 3 | 4 | 6 | |
| 1 | 12 | 23 | 32 | 64 | 100 | 91 | 95 | % |
| 2 | 11 | 34 | 45 | 68 | 120 | 75 | 77 | % |
| 3 | 11 | 32 | 39 | 45 | 68 | 75 | 98 | % |
| 4 | 9 | 32 | 55 | 59 | 80 | 80 | 77 | % |
| 5 | 14 | 34 | 64 | 109 | 131 | 104 | 104 | % |
| 6 | 16 | 66 | 66 | 91 | 98 | 116 | 86 | % |

Optimum results are thus obtained using reaction mixture No. 5 total conversion to p-hydroxyampicillin is complete in 2 hours at an enzyme concentration of 10 mg./ml. and at a pH of 7.0.

EXAMPLE D

The following reaction mixture was prepared containing 50 mg. defatted bran (Shiloh) 2.5 mg. 6-D-(—)-α-amino-α-(p-acetoxyphenylacetamido)penicillanic acid (p-acetoxyampicillin) and 5.0 ml. water. The mixture was shaken at about 28° C. and monitored by chromatography at 1, 2 and 3 hours as described in Example 2.

Results of the biochromatograms indicated at 100% conversion of p-acetoxyampicillin to p-hydroxyampicillin in three hours. The pH of the reaction mixture remained constant at about 5.7 in spite of the absence of buffer.

EXAMPLE E

The following materials were combined: 20 g. defatted bran (Shiloh) 1.0 g. 6-D-(—)α-amino-α-(p-acetoxyphenylacetamido)penicillanic acid (p-acetoxyampicillin) and 2 liters of an 0.01 M. aqueous solution of pH 7.0 potassium phosphate buffer. The resulting mixture was stirred at about 28° C. and sampled every hour as described in Example A.

The biochromatogram assays indicated 100% conversion in 3 hours. The mixture was then centrifuged. The supernatant liquid was collected, adjusted to a pH of 4.0 with hydrochloric acid and lyophilized. The lyophilate was re-assayed as described above and was found to contain approximately 900 mg. of p-hydroxyampicillin.

The lyophilate, 6.0 g., was slurried in 20 ml. of water. To the resulting mixture was added 6 N hydrochloric acid to lower gradually the pH to 2.0. Stirring was continued for another 15 minutes followed by filtering off the solids. The filtrate was treated with 1.0 g. of decolorizing carbon, filtered and the clear filtrate adjusted to a pH of 4.5. Crystallization took place on scratching of the solution and allowed to continue for 1 hour. The crystals were collected on a filter, washed with water and acetone and then dried to afford 180 mg. of 6-D-(—)-α-amino-α-(p-hydroxyphenylacetamido)-penicillanic acid trihydrate, dec. pt. 201° C.

| | | % Theory | % Found |
|---|---|---|---|
| Anal. Calc'd for $C_{16}H_{19}N_3O_5S$: | C | 45.82 | 45.87 |
| | H | 6.01 | 5.71 |
| | N | 10.02 | 10.48 |
| | K.F.H$_2$O | 12.89 | 13.68 |

BIOLOGICAL DATA

In Vivo Activity Data

The median curative doses ($CD_{50}$) in mice against an overwhelmingly lethal challenge of various pathogenic organisms were determined for 6-[D-(—)-α-amino-α-(4-hydroxyphenyl)acetamido]penicillanic acid. The $CD_{50}$ data obtained are reported below in mg./Kg.

| Organism | Route of Administration | $CD_{50}$ (mg./Kg.) |
|---|---|---|
| S. aureus Smith | intramuscular | 0.2 |
|  | oral | 0.9 |
| Sal. enteritidis | intramuscular | 5.4 |
|  | oral | 4.0 |
| K. pneumoniae | intramuscular | 7 |
|  | oral | 7 |
| S. enteritidis | oral | 3.5 |

Oral Absorption Data

Measurement was made of the blood levels obtained in mice upon oral administration of 6-[D-(—)-α-amino-α-(4-hydroxyphenyl)acetamido]-penicillanic acid. In the test four mice were dosed orally with 30 mg./Kg. of compound. The following are the average blood levels obtained:

| Time (hours) | Blood levels (mcg./ml.) |
|---|---|
| 0.5 | 8.1 |
| 1.0 | 4.0 |
| 2.0 | 1.40 |
| 3.5 | 1.1 |

What we claim is:

1. A process for preparing 6-D-(—)-α-amino-α-(p-hydroxyphenylacetamido)penicillanic acid which comprises treating in aqueous solution 6-D-(—)-α-amino-α-(p-acetoxyphenylacetamido)penicillanic acid with an esterase selected from the group comprising human serum, animal serum, citrus esterase, wheat bran, wheat germ, and bacillus subtilis at a pH between about 5.0 and about 7.5 and at a concentration of about 5 to about 10 mg./ml. of esterase per total volume of the aqueous solution 2. A process as claimed in claim 1 which comprises treating in an aqueous solution 6-D-(—)-α-amino-α-amino-α-(p-acetoxyphenylacetamido)penicillanic acid with an esterase selected from the group comprising citrus esterase, wheat bran, and wheat germ at a pH between about 5.0 and about 7.5 at a concentration of about 5 to about 10 mg./ml. of esterase per total volume of the aqueous solution 3. A process as claimed in claim 2 which comprises treating in an aqueous solution 6-D-(—)-α-amino-α-(p-acetoxyphenylacetamido)penicillanic acid with the commercially available esterase, coarse wheat bran, at a pH between 5.5 and 6.0 and in the presence of a buffer at a pH of 7.0 at a concentration of about 10 mg./ml. of esterase per total volume of solution.

* * * * *